United States Patent [19]

Jolly

[11] Patent Number: Plant 6,559

[45] Date of Patent: Jan. 24, 1989

[54] MINIATURE ROSE PLANT NAMED 'ARIZONA SUNSET'

[76] Inventor: Nelson F. Jolly, P.O. Box 188 Gregg Neck Rd., Galena, Md. 21635

[21] Appl. No.: 32,431

[22] Filed: Mar. 30, 1987

[51] Int. Cl.[4] ..... A01H 5/00

[52] U.S. Cl. ..... Plt./7

[58] Field of Search ..... Plt./6-10

*Primary Examiner*—James R. Feyrer

[57] ABSTRACT

A new and distinct variety of rose plant of the miniature rose class, which was originated by my crossing Chris Jolly as seed parent and Party Girl as pollen parent; characterized by brilliant golden yellow and orange-red blended colored flowers of exhibition quality.

1 Drawing Sheet

The present invention relates to a new and distinct variety of rose plant of the miniature rose class, which was originated by my crossing as seed parent the rose known as "Chris Jolly" and the rose known as "Party Girl" (U.S. Plant Pat. No. 4,598) as pollen parent.

Among the novel characteristics possessed by this new variety which distinguished it from all other varieties of which I am aware are:

1. High-centered flowers of unusual multi-color blending of tones of orange-red and deep yellow, with outstanding keeping quality.

2. Relatively large blooms for a miniature, ranging from 1½ to 2", having hybrid tea form of exhibition quality, and borne singly.

3. Vigorous, uniform plant growing to 22-24", with abundant foliage, and good disease resistance.

Asexual reproduction by budding of the new variety as performed in Kent County, Md. shows that the foregoing and other distinguishing characteristics come true to form and are established and transmitted through succeeding propagation.

The new and improved rose variety which I have developed is a brilliant orange-red and golden yellow blended miniature rose that maintains its color well throughout the life of the bloom. The color is outstanding because of the bright orange-red overlay of the yellow petal surface as the flowers open. The flowers come generally one to a stem and are high-centered in form, opening with an exhibition quality. The mass blooming habit makes for an unusual and dramatic color effect as a specimen or edging plant, both as a container-grown or in-ground grown plant. An additional particularly desireable and distinguishing characteristic of my new variety is the good keeping quality of the flowers, which normally last from 12-15 days on the plant and 10-12 days as a cut flower.

The accompanying drawing show typical specimens of the vegetative growth and flowers of the new variety named "Arizona Sunset" (Jolarsun) in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "17-D" is plate 17-D of the Royal Horticultural Society Colour Chart.

Parentage: Seedling.

*Seed parent.*—"Chris Jolly".

*Pollen parent.*—"Party Girl".

Class: Miniature.

The following observations are made of specimens grown outdoors at Kent County, Md., during the month of July.

FLOWER

Blooming habit: Continuous.

A. Bud:

(1) *Size.*—Small.

(2) *Form.*—Pointed and high-centered.

(3) *Color.*—When sepals first divide: near 16-B on the reverse with inner edge of petal brushed with 33-A. When petals begin to unfurl each petal reflects the bright yellow undertones of 16-A with a veined brushed overlay of a blend of orange-red 33-A. This coloration is stable at all stages of the flowering opening.

(4) *Sepals.*—Slightly extended beyond bud.

(5) *Peduncle.*—Length 3.5 cm. Aspect — strong. Strength — erect.

*Color.*—138-A.

B. Bloom:

(1) *Size.*—Average size when fully expanded: 2 inches.

(2) *Borne.*—Singly.

(3) *Form.*—High centered, with petals recurling outward.

(4) *Petalage.*—28-31.

(5) *Color.*—During first two days. Center of flower — near 23-B. Outer petals are 23-C blended to 33-A, washing to 41-A. Base of petals: 16-A. Reverse of petals — 17-D.

(6) *Color change.*—General tonality from a distance — bright yellow with orange-red tonality. Color maintained evenly after three or more days.

C. Petals:

(1) *Texture.*—Medium.

(2) *Appearance.*—Satiny.

(3) *Form.*—Broad, rounded petal with pointed tips.

(4) *Arrangement.*—Regularly arranged shingle-like overlay.

(5) *Petaloids in center.*—Few.

(6) *Persistence.*—Drops off cleanly.

(7) *Fragrance.*—Slight.

(8) *Lasting quality.*—12–15 days on plant, 10–12 days as cut flower.

REPRODUCTIVE ORGANS

A. Stamens, anthers: Irregularly arranged around styles.
(1) *Color.*—Yellow-orange, near to 23-B.
B. Pollen: Color is yellow-orange, near to 22-A.
C. Styles: Regularly arranged, medium length.
D. Stigmas:
*Color.*—Orange-red — 34-A.
E. Hips: Globular, and orange in color.

PLANT

A. Form: Upright and compact.
B. Growth: Very vigorous, with uniform branching.
*Height attained.*—22–24 in.
C. Foliage: Compound of 5–7 leaflets.
(1) *Size.*—Small.
(2) *Quantity.*—Abundant.
(3) *Color.*—New foliage: upper side — 187-A, under side — 148-A. Old foliage: upper side — 137-A, under side — 137-C.
(4) *Shape.*—Oval, pointed.
(5) *Texture.*—Upper side — shiny, smooth. Under side — rough.
(6) *Edge.*—Serrated.

(7) *Serration.*—8 per cm.
(8) *Leaf stem.*—Color — 146-A; under side — 146-A.
(9) *Stipules.*—Short, slightly bearded.
D. Wood:
(1) *New wood.*—Color — 137-C. Bark — smooth.
(2) *Old wood.*—Color — 137-C. Bark — smooth.
E. Thorns:
(1) *Thorns.*—Quantity: On main stalks from base — few; on laterals from stalk — none. Form: Flat base, slightly hooked downward. Length: medium. Color when young — 165-B. Position: Irregular.
(2) *Prickles.*—Quantity: On main stalks — none; on laterals — none.
F. Plant's disease resistance:
(1) *Mildew.*—Moderate.
(2) *Blackspot.*—Moderate.
(3) *Rust.*—None observed.
G. Winter hardiness: Outstanding.

I claim:

1. A new and distinct variety of rose plant of the miniature rose class, substantially as shown and described, characterized particularly by brilliant orange and yellow blended flowers not heretofore reflected so vividly in the color range of the miniature rose class.

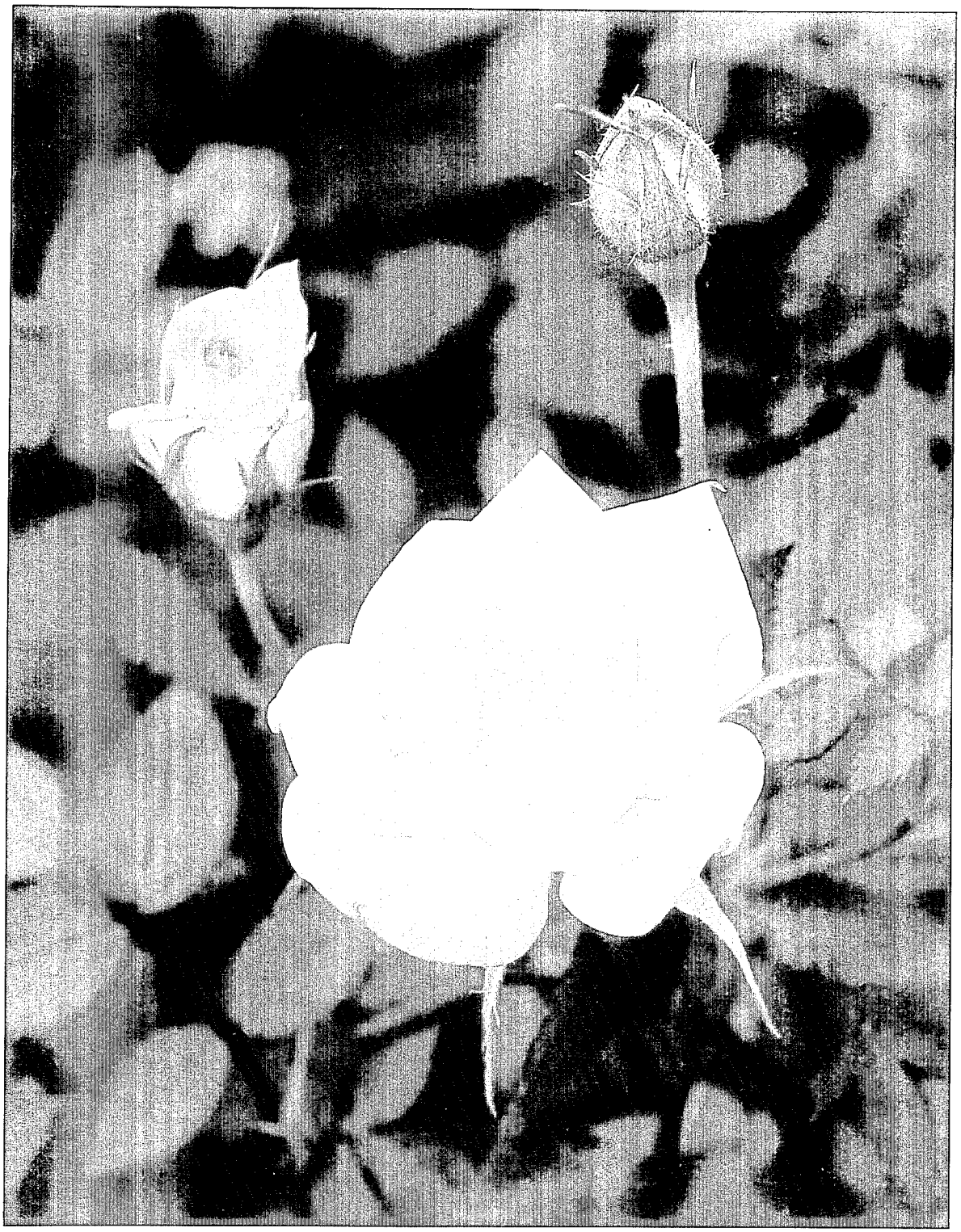

* * * * *